United States Patent [19]

Hannart

[11] 4,029,659
[45] June 14, 1977

[54] N-DISUBSTITUTED AMINOETHYL ESTERS OF 11-METHOXY-RAUBASINIC ACID

[75] Inventor: Jean Alfred Alphonse Joseph Hannart, Brussels, Belgium

[73] Assignee: Omnium Chimique Societe Anonyme, Brussels, Belgium

[22] Filed: July 22, 1974

[21] Appl. No.: 490,436

Related U.S. Application Data

[63] Continuation of Ser. No. 238,818, March 28, 1972, abandoned.

[30] Foreign Application Priority Data

Mar. 29, 1971 Belgium .............................. 764950
Mar. 17, 1972 Belgium .............................. 115227

[52] U.S. Cl. .................. 260/247.2 B; 260/268 PC; 260/293.53; 424/248;255; 424/250; 424/267
[51] Int. Cl.² ........................................ C07D 491/22
[58] Field of Search ............. 260/293.53, 247.2 B, 260/268 PC; 424/267, 248, 250

[56] References Cited

UNITED STATES PATENTS 3,072,664  1/1963  Salkin ........................... 260/293.53
3,104,243  9/1963  Gillo ............................. 260/294.3

Primary Examiner—G. Thomas Todd
Attorney, Agent, or Firm—Pollock, Vande Sande & Priddy

[57] ABSTRACT

N-disubstituted aminoethyl esters of 11-methoxy-raubasinic acid of the formula:

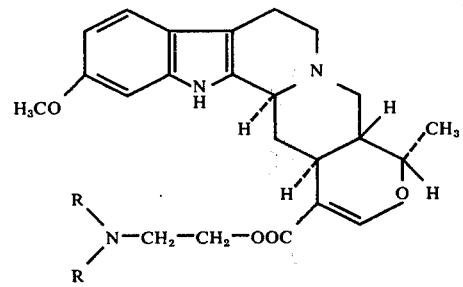

in which R is an alkyl group containing up to 4 carbon atoms or the two R groups, together with the nitrogen atom to which they are attached, form a morpholinyl, piperidinyl, piperazinyl or pyrrolidinyl group, and their physiologically acceptable acid addition salts. The process for the preparation of an N-disubstituted aminoethyl ester of 11-methoxy-raubasinic acid of the formula specified hereinabove, which comprises esterifying 11-methoxy-raubasinic acid with a substituted aminoethyl halide of the formula:

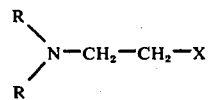

in which X is a halogen atom and R has the meaning specified in claim 1.

9 Claims, 1 Drawing Figure

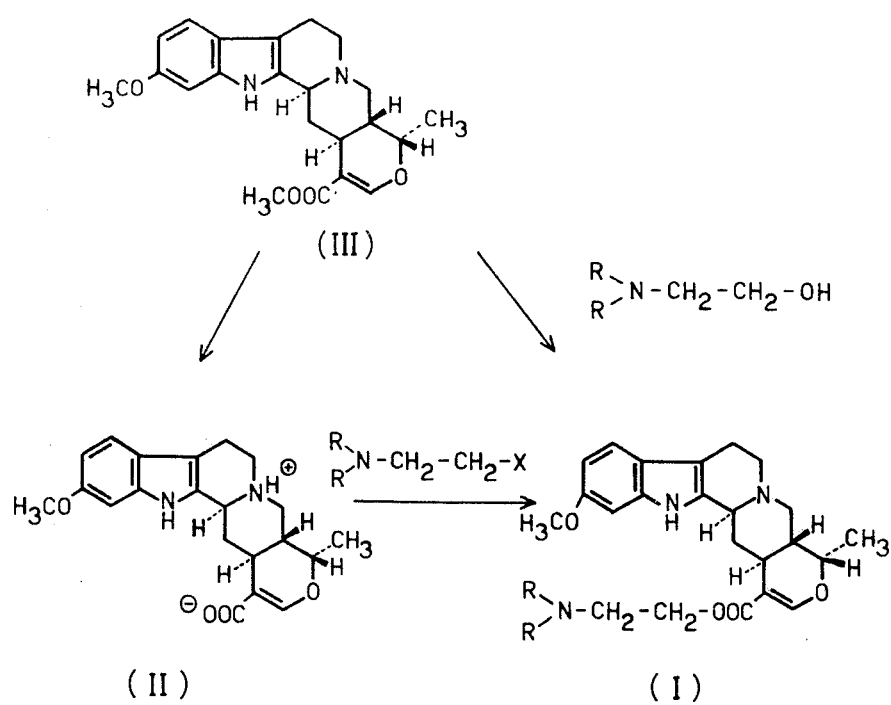

N-DISUBSTITUTED AMINOETHYL ESTERS OF 11-METHOXY-RAUBASINIC ACID

This is a continuation of application Ser. No. 238,818 filed Mar. 28, 1972 now abandoned.

The present invention is concerned with certain novel N-disubstituted aminoethyl esters of 11-methoxy-raubasinic acid and with processes for their preparation.

We have found that N-disubstituted aminoethyl esters of 11-methoxy-raubasinic acid of the formula:

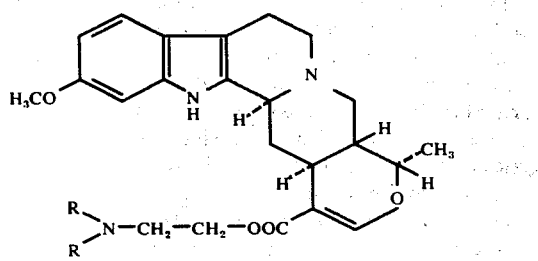

in which R is an alkyl group, preferably containing up to 4 carbon atoms, or the two R groups, together with the nitrogen atom to which they are attached, form a morpholinyl, piperidinyl, piperazinyl or pyrrolidinyl heterocyclic group, and their physiologically acceptable acid addition salts, have valuable pharmacological properties.

The compounds of formula I and their acid addition salts are novel and constitute one aspect of the present invention.

The present invention also comprises pharmaceutical compositions comprising a compound of formula I and an inert, physiologically acceptable carrier.

The compounds according to the invention can be prepared (I) from 11-methoxy-raubasinic acid or (II) from 11-methoxy-raubasine by transesterification; these two processes will be described in turn.

I. Preparation of the esters from 11-methoxy-raubasinic acid 11-methoxy-raubasinic acid, which has the formula:

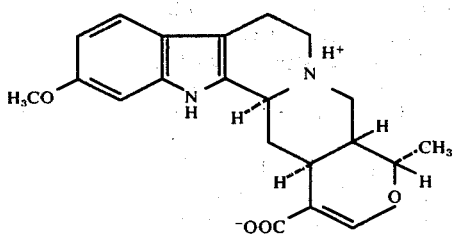

can be obtained by saponification of 11-methoxy-raubasine, which has the formula:

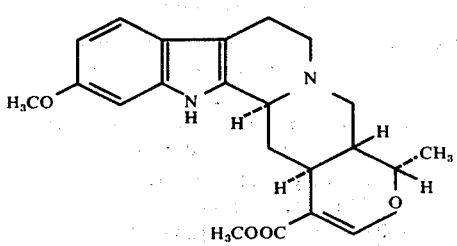

11-methoxy-raubasinic acid can be isolated directly, in the form of a zwitterion, from the saponification mixture by precipitation at the isoelectric pH. The insolubility of the zwitterion in the saponification mixture enables losses of the product to be avoided and the yield to be increased. In addition, the acid is obtained in a high state of purity; inorganic and organic salts remain in solution.

To produce the desired esters, 11-methoxy-raubasinic acid, in the form of the zwitterion, is reacted with a substituted aminoethyl halide of the formula:

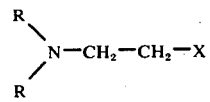

in which R has the above-stated meaning and X is a halogen atom. The reaction is preferably carried out in an organic solvent and in the presence of an alkali metal carbonate which is insoluble in the reaction medium. The reaction is also preferably carried out by heating the reaction mixture to reflux temperature, preferably under an inert atmosphere. Suitable organic solvents are, for example, anhydrous alcohols and, in particular, isopropanol. Other organic solvents which do not dissolve the alkali metal carbonate used, can, however, also be used. The preferred alkali metal carbonate is potassium carbonate. The purpose of the carbonate is to bind the hydrohalic acid, HX, liberated in the course of the reaction. The binding of the liberated acid displaces the reaction equilibrium in the desired sense and increases the yield.

According to a variant of the process, the hydrochloride of the substituted aminoethyl halide, of the formula:

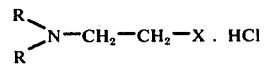

may be directly reacted with an alkali metal salt of 11-methoxy-raubasinic acid in the presence of an acid acceptor which is insoluble in the reaction medium and dry potassium acetate, in a solvent such as isopropanol and, preferably, at the reflux temperature of the solvent. The alkali metal chloride formed is filtrated off and the hydrochloride salt of the desired ester is then precipitated by the addition of gaseous hydrogen chloride or concentrated hydrochloric acid.

The following examples are given by way of illustration only:

EXAMPLE 1

11-methoxy-raubasinic acid

A mixture of a suspension of 18.8 g (0.045 M) of 11-methoxy-raubasine hydrochloride in 668 ml of methanol and a solution of 10.25 g of caustic soda in pastilles in 340 ml of distilled water, was heated to reflux under an inert gas and while protected from light. After boiling for 20 hours, the solution was clear and the alcohol was distilled off under reduced pressure to leave a volume of 250 ml. The aqueous solution remaining was cooled to 20° C and extracted with 100 ml of methylene chloride, and then filtered.

The solution obtained was acidified with 50% aqueous acetic acid to pH 6.5 and it was then placed in a refrigerator. The precipitate obtained was thoroughly drained and washed with a little water. It was drained again and dried for 5 days over $P_2O_5$. 16.2 g of a strictly anhydrous product were obtained; yield 98.2%.

Characteristics: insoluble in water at pH 6–6.5, soluble in acidic and alkaline media, soluble in alcohol and methylene chloride, crystallisable in isopropanol, m.p. 250° C.

EXAMPLE 2

Dimethylaminoethyl 11-methoxy-raubasinate dihydrochloride 1.85 g (0.005 M) of 11-methoxy-raubasinic acid, 50 ml of anhydrous isopropanol, 0.55 g (0.006 M) of anhydrous $Na_2CO_3$, and 0.64 g (0.006 M) of dimethylaminoethyl chloride were heated to reflux temperature under argon for 5 hours. The zwitterion passed slowly into solution. The precipitate present in the reaction mixture was filtered off and washed with a little dry isopropanol, and the filtrate was acidified with isopropanol saturated with gaseous HCl. A precipitate was formed which, after draining and drying, weighed 1.75 g; yield 67.8%.

The product was recrystallised from methanol.

By adding isopropanol to the crystallisation mother liquor, then evaporating off the methanol and allowing the mixture to stand in a refrigerator, a second crop readily crystallised. M.p. > 310° C (decomp).

U.V. absorption: the product showed maxima at 226 m$\mu$ and 294 m$\mu$

I.R. absorption: ester carbonyl at 1725 cm$^{-1}$

| Analysis : | C % | H % | N % | Cl % |
|---|---|---|---|---|
| Calculated (for $C_{25}H_{35}N_3O_4Cl_2$) | 58.59 | 6.88 | 8.19 | 13.83 |
| Found | 58.39 | 6.92 | 8.09 | 13.68 |

EXAMPLE 3

Dimethylaminoethyl 11-methoxy-raubasinate dihydrochloride

1 Mole (406.53 g) of anhydrous potassium 11-methoxy-raubasinate was dissolved in 4 liters of absolute isopropanol in a flask provided with an agitator, a cooling condenser provided with a caustic soda quard, and a thermometer. 0.1 Mole (9.8 g) of dry potassium acetate, and then 1.3 mole (179.7 g) of dry and finely pulverised potassium carbonate were then added.

The suspension obtained was then cooled to between 5° and 10° C by placing the flask in an ice bath and 1.1 mole (158.4 g) of β-dimethylaminoethyl chloride hydrochloride was added in small portions. When the addition was complete, the suspension was heated to reflux temperature and maintained at that temperature for 5 hours. The reaction mixture was then cooled and filtered. The solid residue was washed with about 100 ml of isopropanol.

2 Moles (64 g) of absolute methanol were added to the filtrate and then an ice-cold solution of anhydrous hydrochloric acid in isopropanol was added until a pH of about 2 was obtained. A pale yellow precipitate was formed. It was left to stand in suspension overnight at a temperature of from −10° to −15° C and was then filtered off. The yellow solid was recrystallised from a methanol-isopropanol mixture.

The product had the same characteristics as that of Example 2.

II. Preparation of the esters from 11-methoxy-raubasine by transesterfication.

This method enables the esters to be obtained in a single stage in good yields and reasonably short reaction times.

The starting material is 11-methoxy-raubasine (III). Transesterification is preferably carried out in the presence of a catalyst, suitable catalysts being, for example, alkali metal alcoholates, of which it is preferred to use an alcoholate of the substituted aminoalcohol used as one of the reactants or sodium methylate. The reaction is preferably carried out in an organic solvent, such as an aromatic hydrocarbon. The methanol formed in the course of the reaction can be removed by the use of a molecular sieve since the latter can, in general, absorb straight chain lower alcohols. In this way, the equilibrium of the reaction is displaced in the desired sense and the yield improved. The molecular sieve can, of course, be replaced by any other means of binding the methanol produced. The reaction is preferably carried out under an inert atmosphere.

The product can be isolated by washing the organic phase with water in order to remove the unreacted alcohol, then drying the organic phase over sodium sulphate, and evaporating the dried organic phase to dryness under reduced pressure. The residue thus obtained may, for example, be dissolved in an organic solvent and treated with dry gaseous hydrogen chloride or concentrated hydrochloric acid in order to obtain the hydrochloride salt of the desired ester.

The following examples are given by way of illustration only:

EXAMPLE 4

Morpholinoethyl 11-methoxy-raubasinate dihydrochloride 0.23 g of sodium was added to a solution of 1.31 g of 2-morpholino-ethanol in 150 ml of dry benzene. 3.82 g of 11-methoxy-raubasine were added to the mixture obtained and the mixture was heated to reflux under a nitrogen atmosphere and while shielded from light, for 7 hours. The reaction mixture was then cooled and washed with water. The benzene phase was then dried over anhydrous sodium sulphate and evaporated to dryness under reduced pressure. The residue was dissolved in isopropanol and the solution was acidified with gaseous hydrogen chloride; the desired compound precipitated. M.p. 286°–7° C.

$[\alpha]_D = -23°$ (c = 1, $H_2O$)

U.V. λ max at 228 and 296 m$\mu$

I.R. ester carbonyl at 1725 cm$^{-1}$

Analysis: % Cl. calculated: 13.11%; found: 13.02%.

EXAMPLE 5

Morpholinoethyl 11-methoxy-raubasinate dihydrochloride

The reaction was carried out in a Soxhlet apparatus. 3.8 g of 11-methoxy-raubasine, 1.31 g of 2-morpholino-ethanol, 0.23 g of sodium, and 150 ml of benzene were introduced into the flask of the apparatus. 10 g of a molecular sieve of the 4 A type were placed in the filter paper cartridge of the apparatus. The mixture was heated to reflux under a current of nitrogen. When the transesterification was complete, the mixture was cooled and washed with water, the benzene phase was separated, dried over anhydrous sodium sulphate, and evaporated to dryness under reduced pressure. The residue obtained was dissolved in isopropanol and acidified with gaseous hydrogen chloride. The desired compound was precipitated. It had the same characteristics as the product of Example 4.

EXAMPLES 6-8

The following compounds were prepared by either one of the processes described above.

EXAMPLE 6

Piperidinoethyl 11-methoxy-raubasinate hydrochloride m.p. 252° C (dec.)
$[\alpha]_D$ −23° (c = 1, $H_2O$)
U.V.: λ max at 226 and 295 mμ
I.R.: ester carbonyl at 1724 $cm^{-1}$

| Analysis : | C % | H % | N % |
|---|---|---|---|
| Calc. for | | | |
| $C_{28}H_{39}O_4N_3Cl_2$ | 60.86 | 7.11 | 7.60 |
| Found | 60.84 | 7.08 | 7.63 |

EXAMPLE 7

Pyrrolidinoethyl 11-methoxy-raubasinate hydrochloride
m.p. 230° C
$[\alpha]_D$ −21° (c = 1, $H_2O$)
U.V.: λ max at 227 and 296 mμ
I.R.: ester carbonyl at 1725 $cm^{-1}$

| Analysis : | C % | H % | N % |
|---|---|---|---|
| Calc. for | | | |
| $C_{27}H_{37}O_4N_3Cl_2$ | 62.06 | 7.13 | 8.04 |
| Found | 62.10 | 7.03 | 8.11 |

EXAMPLE 8

N-methyl-piperazinoethyl 11-methoxy-raubasinate hydrochloride
m.p. > 295° C
$[\alpha]_D$ −20° (c = 1, $H_2O$)
U.V.: λ max at 226 and 294 mμ
I.R.: ester carbonyl at 1725 $cm^{-1}$

| Analysis : | C % | H % | N % |
|---|---|---|---|
| Calc. for | | | |
| $C_{28}H_{41}O_4N_4Cl_3$ | 55.67 | 6.84 | 9.27 |
| Found | 55.63 | 6.79 | 9.32 |

What we claim is:
1. N-disubstituted aminoethyl ester of 11-methoxy-raubasinic acid of the formula :

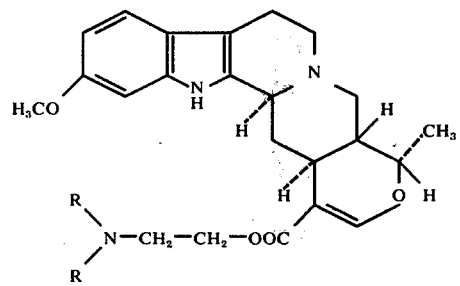

in which R is an alkyl group containing up to 4 carbon atoms or the two R groups, together with the nitrogen atom to which they are attached, form a morpholinyl, piperidinyl, piperazinyl or pyrrolidinyl group, and their physiologically acceptable acid addition salts.
2. The ester of claim 1 wherein both R groups are methyl.
3. The hydrochloride addition salt of the ester of claim 2.
4. The ester of claim 1 wherein both R groups together with the nitrogen atom to which they are attached form a morpholinyl group.
5. The hydrochloride addition salt of the ester of claim 4.
6. The ester of claim 1 wherein both R groups together with the nitrogen atom to which they are attached form a piperidinyl group.
7. The hydrochloride addition salt of the ester of claim 6.
8. The ester of claim 1 wherein both R groups together with the nitrogen atom to which they are attached form a pyrrolidinyl group.
9. The hydrochloride salt of the compound of claim 8.

* * * * *